(12) United States Patent
Whitsett

(10) Patent No.: US 12,714,600 B2
(45) Date of Patent: Aug. 25, 2026

(54) VITRECTOR AND METHOD FOR PERFORMING A ONE-STEP POSTERIOR VITRECTOMY USING THE SAME

(71) Applicant: Vista Ophthalmics, LLC, Katy, TX (US)

(72) Inventor: Jeffrey Whitsett, Houston, TX (US)

(73) Assignee: Vista Ophthalmics, LLC, Katy, TX (US)

( * ) Notice: Subject to any disclaimer, the term of this patent is extended or adjusted under 35 U.S.C. 154(b) by 723 days.

(21) Appl. No.: 17/519,150

(22) Filed: Nov. 4, 2021

(65) Prior Publication Data

US 2022/0054313 A1 Feb. 24, 2022

Related U.S. Application Data

(63) Continuation-in-part of application No. 16/812,314, filed on Mar. 8, 2020, now Pat. No. 11,684,512.

(Continued)

(51) Int. Cl.
*A61F 9/007* (2006.01)
*A61B 17/00* (2006.01)

(52) U.S. Cl.
CPC .................... *A61F 9/00754* (2013.01); *A61B 2017/00544* (2013.01); *A61B 2217/005* (2013.01)

(58) Field of Classification Search
CPC .. A61F 9/00736; A61F 9/00763; A61F 9/007; A61F 9/00709; A61F 9/00745;

(Continued)

(56) References Cited

U.S. PATENT DOCUMENTS 4,331,130 A 5/1982 Lewicky
5,487,725 A * 1/1996 Peyman .............. A61F 9/00763 604/521

(Continued)

FOREIGN PATENT DOCUMENTS

| | | |
|---|---|---|
| JP | 2015-531266 | 11/2015 |
| JP | 2018-537214 | 12/2018 |
| WO | WO 2019/069198 | 4/2019 |

OTHER PUBLICATIONS

Wong, Randall, “27 gauge Vitrectomy for ERM and FOV”, Nov. 8, 2015, YouTube video, <https://www.youtube.com/watch?v=Dla_Dn2fIZE> (Year: 2015).*

(Continued)

*Primary Examiner* — Diane D Yabut
*Assistant Examiner* — Christian D Knauss
(74) *Attorney, Agent, or Firm* — Fish & Richardson P.C.

(57) ABSTRACT

A vitrector for removing material from an eye includes a hand piece, a shaft coupled at a first end to a first end of the hand piece, the shaft having a sharp second end opposite the first end of the shaft, and a cutting device positioned within the shaft and configured for removing the material from the eye. The sharp second end of the shaft is configured for piercing a pars plana of the eye and a sclera of the eye. A method for removing material from an eye includes forming a single opening through a pars plana of the eye and a sclera of the eye using a sharp point of a shaft of a vitrector, cutting the material using a cutting device incorporated within the shaft, and removing the material from the eye using the vitrector.

20 Claims, 3 Drawing Sheets

Related U.S. Application Data

(60) Provisional application No. 62/843,225, filed on May 3, 2019.

(58) Field of Classification Search
CPC .. A61F 9/00754; A61F 2/1662; A61F 2/1664; A61F 2/1667; A61F 2/167; A61F 2/1672; A61F 2/1675; A61F 2/1678
See application file for complete search history.

(56) References Cited

U.S. PATENT DOCUMENTS 5,716,363 A * 2/1998 Josephberg ......... A61F 9/00763 606/171
5,792,103 A 8/1998 Schwartz et al.
8,888,802 B2 11/2014 Underwood et al.
9,060,841 B2 6/2015 McCawley
9,101,442 B2 8/2015 McDonell
9,498,377 B2 11/2016 McCary et al.
9,498,378 B2 * 11/2016 McDonell ........... A61F 9/00736
9,750,639 B2 9/2017 Barnes et al.
10,376,414 B2 8/2019 Hallen et al.
2009/0137993 A1 5/2009 Kurtz
2009/0259242 A1 * 10/2009 Gerg .................. A61F 9/00736 606/167
2011/0054508 A1 3/2011 Zhou et al.
2014/0074011 A1 3/2014 Charles
2014/0257257 A1 9/2014 Grant et al.
2016/0166433 A1 6/2016 Czaja
2017/0165114 A1 * 6/2017 Hallen ................ A61F 9/00736
2018/0311074 A1 11/2018 Heeren
2020/0345548 A1 11/2020 Whitsett

OTHER PUBLICATIONS

Roybal, "Indirect Ophthalmoscopy 101," May 15, 2017, American Academy of Ophthalmology, retrieved on Sep. 7, 2022, retrieved from URL <https://www.aao.org/young-ophthalmologists/yo-info/article/indirect-ophthalmoscopy-101>, 5 pages.
Ohji et al., "New Instruments in Vitrectomy," Vitreo-retinal Surgery, 2007, 85-98.
Schonfeld, "23- vs 20-gauge pars plana vitrectomy in combination with bimanual microincisional cataract surgery (b-MICS) for the treatment of macular hole and cataract as a one-step procedure," Eye, Jun. 27, 2013: 952-958.
Chen et al., [online], "Surgery for Eye Floaters (Massive)—Vitrectomy for eye floaters—Dr Simon Chen," Feb. 25, 2017, Internet Archive: Wayback Machine URL <https://web.archive.org/web/20240421013326/https://www.youtube.com/watch?v=1HaG3Cktq5k>, retrieved on Jan. 23, 2026, retrieved from URL <https://www.youtube.com/watch?v=1HaG3Cktq5k>, 11 pages.

* cited by examiner

VITRECTOR AND METHOD FOR PERFORMING A ONE-STEP POSTERIOR VITRECTOMY USING THE SAME

CROSS-REFERENCE TO RELATED PATENT APPLICATIONS

This application is a continuation-in-part of, and claims priority to, U.S. application Ser. No. 16/812,314, filed Mar. 8, 2020, which claims priority to U.S. Provisional Application Ser. No. 62/843,225, filed on May 3, 2019, each of which is herein incorporated by reference.

TECHNICAL FIELD

The present disclosure relates generally to medical equipment, and more particularly to a new and improved vitrector and a method for performing a one-step posterior vitrectomy within a patient's eye.

BACKGROUND

Conventionally, a posterior vitrectomy has been accomplished by means of a three port procedure to remove floaters from the eye, as is generally indicated by the reference character 100 in FIG. 1. In order to allow access to the pars plana of the sclera using this convention three port procedure, initially the conjunctiva is incised and folded back so as to expose the sclera and pars plana. Irrigation is initiated by means of a cannula inserted into the eye of the patient through means of a first port formed within the eye by means of an MVR blade so as to maintain physiologic pressure inside the vitreous cavity. This irrigation port is placed and sutured to the sclera, although such is not shown in FIG. 1. Two additional ports are also created through the pars plana by means of an MVR blade so as to allow access for additional instrumentation including a light pipe 102 for visualization, and a pneumatic guillotine cutter for vitreous removal which is incorporated within a conventional, blunt-tipped vitrector 104. After the procedure, the entry ports are closed with absorbable sutures so as to maintain water-tight integrity of the vitreous cavity.

SUMMARY

Briefly, the present disclosure comprises the development of a one-step vitrector, which is an advancement in the art in providing access to anterior and mid vitreous debris. In particular, the embodiments described herein enable removal of material from the vitreous cavity of the patient's eye by an anterior segment surgeon at the time of cataract surgery. Floaters within the vitreous cavity occur over time as the process of vitreous aging (syneresis) changes the dynamics in the vitreous cavity. As this process occurs, the syneretic vitreous places pressure upon posterior vitreous attachments, causing them to break free and subsequently lodge within the anterior vitreous space and/or the mid vitreous space. These floaters can range in size from small and visually insignificant, to large and visually quite distracting. Classic management of this condition has been observation, with natural adaptation and the long term break down of the floater. Oftentimes, patients have to move their eye to shift the floater while performing simple activities as driving and reading. The ability to remove significant floaters at the time of cataract surgery using the embodiment described herein will allow the patient to have visual improvement with minimal if any additional surgical time and morbidity.

In one aspect, a vitrector for removing material from an eye includes a hand piece, a shaft coupled at a first end to a first end of the hand piece, the shaft having a sharp second end opposite the first end of the shaft, and a cutting device positioned within the shaft and configured for removing the material from the eye. The sharp second end of the shaft is configured for piercing a pars plana of the eye and a sclera of the eye.

Embodiments can include one or more of the following features in any combination.

In certain embodiments, a diameter of the shaft is approximately 27 gauge.

In some embodiments, the shaft has a length of between 0.5 inches and 0.5625 inches.

In certain embodiments, the cutting device is a pneumatically driven guillotine cutter.

In some embodiments, the pneumatically driven guillotine cutter is fluidly coupled to a source of pneumatic air for driving the pneumatically driven guillotine cutter.

In certain embodiments, the vitrector further includes a pneumatic line configured to fluidly couple the cutting device to the source of pneumatic air.

In some embodiments, the pneumatic line is coupled to a second end of the hand piece opposite the first end of the hand piece.

In certain embodiments, the vitrector further includes an aspiration line fluidly coupled to the cutting device, and removing the material from the eye includes drawing the material through the aspiration line.

In some embodiments, the aspiration line is coupled to a second end of the hand piece opposite the first end of the hand piece.

In certain embodiments, the aspiration line is fluidly coupled to a source of suction.

In some embodiments, the shaft includes an elongate body coupled at a first end to the first end to the hand piece, and the sharp second end of the shaft includes a needle tip coupled to a second end of the elongate body opposite the first end of the elongate body.

In certain embodiments, the material includes one or more vitreous floaters, and the cutting device is configured to sever the one or more vitreous floaters from a vitreous cavity of the eye.

In another aspect, a method for removing material from an eye includes forming a single opening through a pars plana of the eye and a sclera of the eye using a sharp point of a shaft of a vitrector, cutting the material using a cutting device incorporated within the shaft, and removing the material from the eye using the vitrector.

Embodiments can include one or more of the following features in any combination.

In certain embodiments, the method further includes fluidly coupling a source of pneumatic air to the cutting device.

In some embodiments, the cutting device includes a pneumatically driven guillotine cutter, and cutting material from the eye using the cutting device includes pneumatically driving the pneumatically driven guillotine cutter using the source of pneumatic air.

In certain embodiments, the method further includes fluidly coupling an aspiration line to the cutting device.

In some embodiments, removing the material from the eye using the vitrector includes drawing the material through the aspiration line In certain embodiments, the material includes one or more floaters; and removing the material from the eye using the vitrector includes removing the one or more floaters from a vitreous cavity of the eye.

In some embodiments, the method further includes prior to forming a single opening through the pars plana of the eye and sclera of the eye, implanting an intraocular lens in the eye In certain embodiments, the intraocular lens is implanted in the eye during a cataract surgery.

In accordance with the principles and teachings of the present disclosure, the new and improved vitrector includes a tubular shaft portion which is attached to a distal end of a vitrector hand piece. In addition, the shaft portion is provided with a sharply pointed needle tip portion for piercing the pars plana and sclera of the eye, and a pneumatically driven guillotine cutter is incorporated within the shaft portion of the vitrector at a location immediately adjacent to the sharply pointed needle tip portion. A source of pneumatic air is operatively connected to the proximal end of the vitrector hand piece and is pneumatically connected to the guillotine cutter so as to drive the same. In addition, an aspiration line is also operatively connected to the proximal end of the vitrector hand piece and is also fluidly connected to the region immediately adjacent to the pneumatically driven guillotine cutter so as to remove the floater particles severed from the vitreous cavity using the pneumatically driven guillotine cutter by aspiration.

An overall objective of the present disclosure is to provide a new and improved vitrector and a method for performing a vitrectomy. Another overall objective of the present disclosure is to provide a new and improved vitrector and a method for performing a vitrectomy wherein the entire procedure can be radically simplified. Still another overall objective of the present disclosure is to provide a new and improved vitrector and a method for performing a vitrectomy wherein the entire procedure can be radically simplified, can be significantly shortened in duration, and can be less bothersome to the patient. Yet another overall objective of the present disclosure is to provide a new and improved vitrector and a method for performing a vitrectomy wherein the entire procedure is radically simplified, can be significantly shortened in duration, and can be less bothersome to the patient. Yet still another overall objective of the present disclosure is to provide a new and improved vitrector and a method for performing a vitrectomy wherein the entire procedure is radically simplified, can be significantly shortened, and can be less bothersome to the patient as a result of reducing the number of incisions that need to be made within or through various regions of the eye. A further overall objective of the present disclosure is to provide a new and improved vitrector and a method for performing a vitrectomy wherein the entire procedure is radically simplified, can be significantly shortened, and can be less bothersome to the patient as a result of reducing the number of incisions that need to be made within or through various regions of the eye in order to accommodate the various different medical instruments or components currently required to perform a conventional vitrectomy. Another objective of the present disclosure is to provide a new and improved vitrector and a method for performing a vitrectomy that does not require the use of sutures. Another objective of the present disclosure is to provide a new and improved vitrector and a method for performing a vitrectomy that increases patient safety.

Various other aspects, features, and attendant advantages of the present disclosure will be apparent from the description and drawings, and from the claims.

DESCRIPTIONS OF DRAWINGS

DETAILED DESCRIPTION

Figure 1:
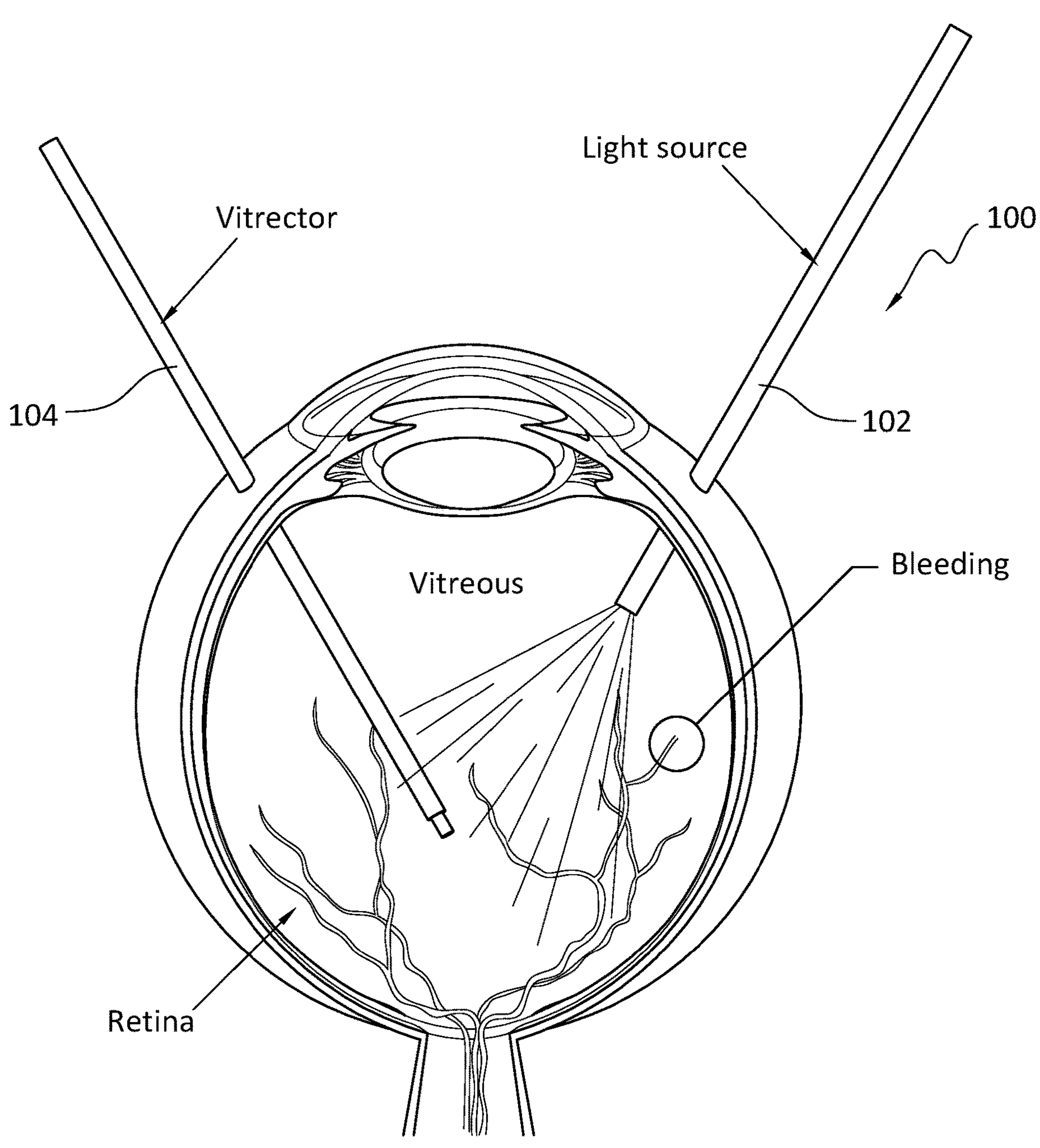
FIG. 1 is a schematic cross-sectional view of the human eye wherein a conventional, PRIOR ART system of medical instruments and other components are utilized in order to perform a conventional vitrectomy.

Before proceeding with the detailed description of the present disclosure, it may be helpful to initially understand several medical terms which relate to the various regions of the eye in connection with which a vitrectomy is to be performed by means of the cataract surgeon, whereby the performance of the vitrectomy will be better understood:

For example, the VITREOUS comprises a transparent colorless gel that fills the posterior chamber of the eye. The vitreous is composed of water, collagen and hyaluronic acid.

FLOATERS are spots in your vision that are lodged within the vitreous. Most eye floaters occur as a result of an aging phenomenon wherein the gel fluid changes over time. Microscopic fibers congeal and become lodged within the vitreous gel. If located centrally, they can cast shadows upon the retina and thereby cause obstructions to one's vision.

POSTERIOR VITREOUS DETACHMENT is a naturally occurring process wherein, as the vitreous gel changes, the attachment to the eye becomes detached and moves into the vitreous cavity.

The SCLERA comprises the outer covering of the eyeball which is composed of collagen and elastic fibers.

The CORNEA comprises the transparent layer that covers the front part of the eye. The primary function of the cornea is to refract or bend light.

A VITRECTOMY is a surgical procedure which removes vitreous gel and functional abnormalities through a small port system incised into the eyeball.

The VISCOELASTIC is a clear viscous substance comprised of sodium hyaluronate which is used in ocular surgery to maintain space, and to protect ocular structures.

An IOL is an intraocular lens, an artificial lens, which is implanted at the time of cataract surgery so as to help bend light and focus it upon the retina. An IOL replaces one's original lens when, due to aging, the original lens becomes cloudy or progressively opaque, thereby rendering normal vision virtually impossible and not correctable by means of glasses, contact lenses, or the like.

VITREOUS SYNERESIS is a naturally occurring process, as we age, in which the composition of the vitreous cavity changes so that its content comprises a greater percentage of water content. It is generally a precursor of posterior vitreous detachment.

The PARS PLANA is an area of the sclera, approximately 3-4 mm posterior to the surgical limbus and a common entry site for the entry or insertion of surgical instruments into the posterior vitreous.

Having described the problems or difficulties encountered in connection with the performance of a conventional vitrectomy, and having further defined the various regions of the eye and the various conditions that can affect the eye, it is time to fully disclose the vitrector of the present disclosure. In accordance with the principles and teachings of the present disclosure, and as disclosed within FIGS. 2 and 3, cataract surgery is performed in the usual manner, and after the intraocular lens (IOL) is implanted, the cohesive viscoelastic is refilled or retained within the anterior chamber. The primary incision and the paracentesis are hydrated so as to prevent the collapse of the anterior chamber while the one-step vitrectomy is performed. Adequate dilation is mandatory for the procedure as it is important to visualize the tip and one-step cutter at all times. After the anterior chamber is refilled with viscoelastic material, a caliper is used to measure 3-3.5 mm posterior to the surgical limbus. Using counter-traction, a tubular shaft portion 206 of the one-step vitrector 204 is inserted through the conjunctiva and pars plana, and into the vitreous cavity with the needle tip portion 208 of the vitrector 204 aimed toward the mid vitreous, under constant visualization, behind the intraocular lens (IOL) 205. This is the location where the anterior and mid vitreous floaters will be located and removed.

Figure 2:
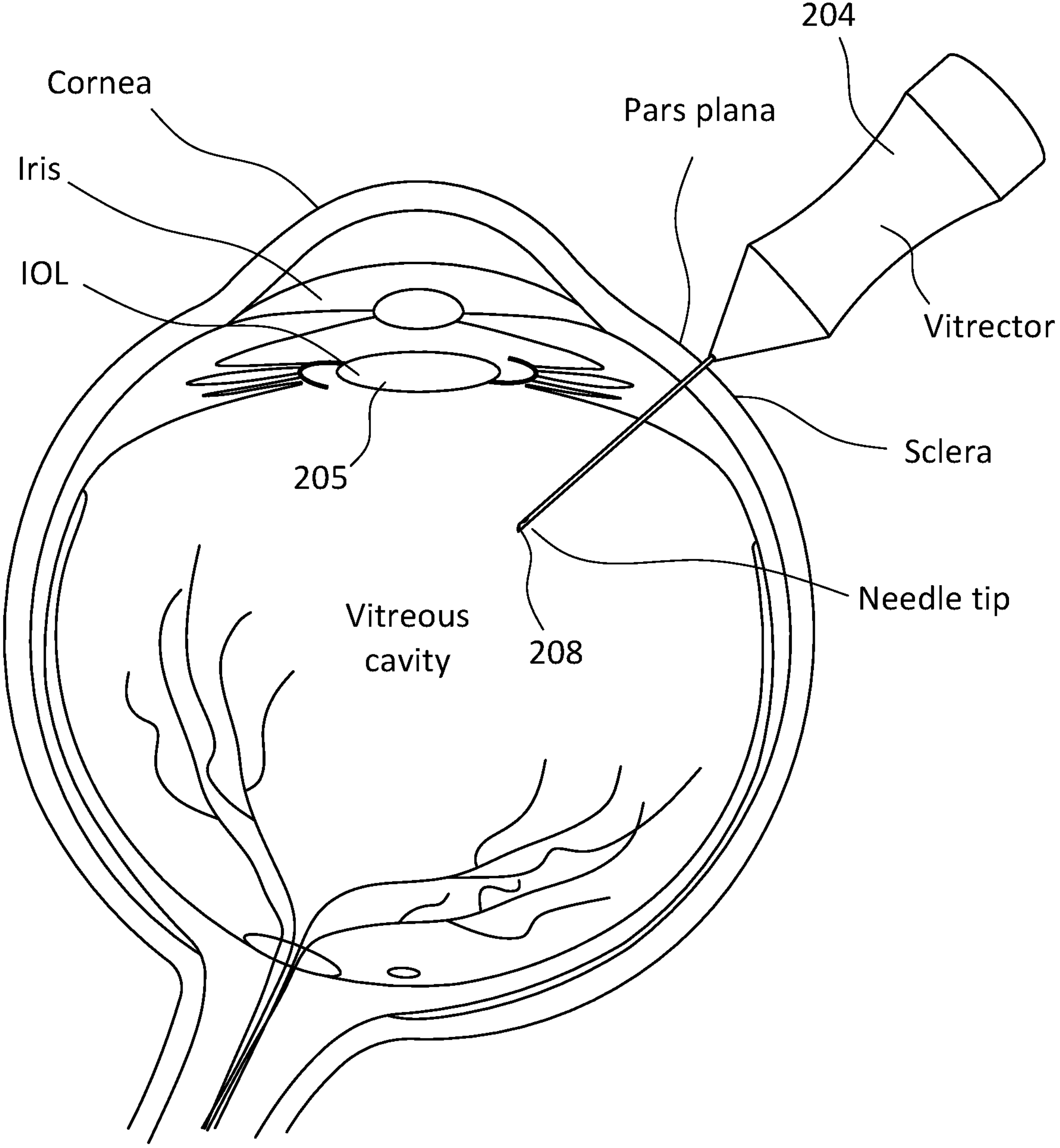
FIG. 2 is a schematic cross-sectional view of the human eye, illustrating, a vitrectomy being performed utilizing the new and improved vitrector of the present disclosure and in accordance with the new and improved method of performing a vitrectomy.
Figure 3:
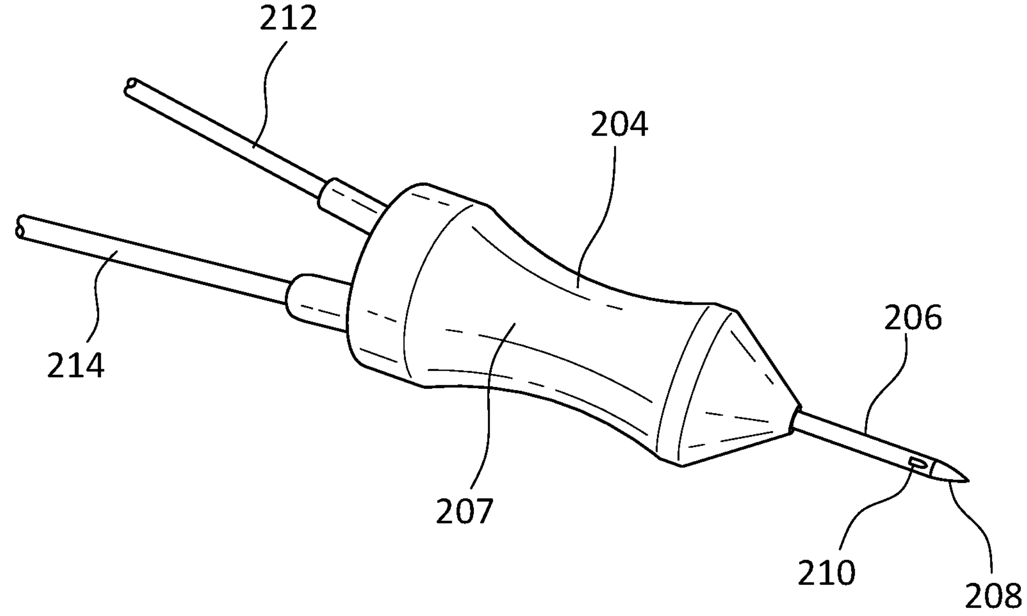
FIG. 3 is a schematic view of the new and improved vitrector of the present disclosure illustrating the various components thereof.

As can best be seen or appreciated from FIG. 3, in addition to FIG. 2, in lieu of the conventional, prior art vitrector, which has a blunt tip or end portion, the new and improved vitrector 204 comprises a tubular shaft portion 206 which is approximately 27 gauge in diameter and approximately one half inch (0.5000") to nine-sixteenths of an inch (0.5625") in length such that the tubular shaft portion 206 of the vitrector 204 has the inherent stiffness required for the procedure. The shaft portion 206 is attached to the distal end portion of a vitrector hand piece 207. In addition, the shaft portion 206 of the vitrector 204 is provided with a sharply pointed needle tip portion 208 for piercing the pars plana and sclera of the eye, and a pneumatically driven guillotine cutter 210 is incorporated within the shaft portion 206 of the vitrector 204 immediately adjacent to the sharply pointed needle tip portion 208.

A source of pneumatic air is operatively connected to the proximal end of the vitrector hand piece 207 through a pneumatic line 212 and is adapted to be fluidly connected to the pneumatically driven guillotine cutter 210 so as to drive the guillotine cutter 210. In a similar manner, an aspiration line 214 is also operatively connected to the proximal end of the vitrector hand piece 207 and is also fluidly connected to the region immediately adjacent to the pneumatically driven guillotine cutter 210 so as enable removal floater particles, which are severed from the vitreous cavity using the pneumatically driven guillotine cutter 210 and are removed from the eye by means of aspiration through the aspiration line 214. In some implementations, the pneumatic line 212 and the aspiration line 214 are each connected to a device that provides pneumatic air and suction to the pneumatic line 212 and the aspiration line 214, respectively, such as a phacoemulsification machine.

After adequate removal of floater particles from the vitreous cavity has been performed under visualization, the vitrector 204 is removed and gentle pressure is applied to the eye with a cotton tip applicator. The viscoelastic is then removed from the anterior chamber in the usual fashion, whereby the pressure within the anterior chamber of the eye is restored to its normal physiological level using a balanced saline solution.

It is noted that in some cases no additional illumination is required when performing vitrectomy using the vitrector 204 in view of the fact that the anterior vitreous can be easily visualized through the dilated pupil of the eye and the intraocular lens (IOL) 205.

The design of the vitrector 204 enables a surgeon to perform vitrectomy through the pars plana without the need to create a peritomy in the conjunctiva or suture the sclera. For example, as described above, the sharp tip portion 208 of the vitrector 204 allows for a sclerotomy to be performed without removal of the conjunctiva or prior insertion of a trocar. In addition, in some implementations, the diameter of the shaft portion 206 of the vitrector 204 is sized to enable the vitrector 204 to be inserted into and removed from the patient's eye without requiring sutures to close the sclerotomy formed by tip portion 208 the vitrector 204.

While certain embodiments have been described, other embodiments are possible.

For example, the vitrector 204 can be used to perform vitrectomy as part of a variety of different cataract procedures. For instance, rupture of the posterior capsule of the eye is a potential complication of standard cataract surgery, and the vitrector 204 can be used to perform anterior vitrectomy following inadvertent rupture of the posterior capsule during cataract surgery. In addition, the vitrector 204 can be used to perform vitrectomy as part of complex cataract surgery, such as surgery for traumatic cataract, in which vitreous material is already present in the anterior chamber or in which there is a high likelihood of vitreous material being present in the anterior chamber during surgery. In addition, the vitrector 204 can be used during pediatric cataract surgeries to perform vitrectomy in pediatric patients as part of the cataract surgery. For pediatric cataract surgeries in which a posterior capsulotomy is planned, the vitrector 204 can be used to remove a portion of the posterior capsule of the patient's eye.

In addition, while the vitrector 204 has been described as being used to perform vitrectomy as part of cataract surgery, the vitrector 204 may be used to perform vitrectomy as part of other types of ocular procedures. For example, the vitrector 204 can be used to perform vitrectomy as part of complex intraocular lens surgery in which vitreous material is already present in the anterior chamber or in which there is a high likelihood of vitreous material being present in the anterior chamber during surgery, such as during an intraocular lens exchange or secondary intraocular lens implantation. For instance, after placement of the IOL during an intraocular lens exchange or secondary intraocular lens implantation, the tubular shaft portion 206 of the one step vitrector 204 can inserted into the vitreous cavity with the needle tip portion 208 of the vitrector 204 aimed behind the intraocular lens 205 and the vitrector 204 can be used to remove anterior and mid vitreous floaters, as described in detail above. In some implementations, the vitrector 204 is used to perform vitrectomy as part of anterior segment reconstruction surgery. Anterior segment reconstruction can be a complex surgery involving several procedures, such as iris repair, lysis of adhesions, and IOL repositioning, and vitrectomy is also often required during anterior segment reconstruction. The vitrector 204 can be used to perform vitrectomy as part of the anterior segment reconstruction surgery.

In addition, while the vitrector 204 has been described as being used to perform vitrectomy as part of or during the course of another ocular surgery, such as cataract surgery or intraocular lens surgery, in some implementations, the vitrector 204 is used to remove vitreous floaters in a vitrectomy procedure that performed independently of any other ocular procedures. For example, as described in detail above, when used during cataract surgery, the vitrector 204 is inserted into the patient's eye after implantation of an IOL. However, the vitrector 204 can alternatively be used to remove vitreous floaters from the patient's eye without requiring implantation of an IOL or performance of any other surgical procedures. For example, in order to perform a vitrectomy without performing other ocular surgeries, the tubular shaft portion 206 of the one step vitrector 204 can simply be inserted through the conjunctiva and pars plana of the eye, and into the vitreous cavity with the needle tip portion 208 of the vitrector 204 aimed toward the mid vitreous and anterior, and mid vitreous floaters can be removed from the vitreous cavity using the cutter 210 of the vitrector, as described in detail above. The design of the one-step vitrector 204 provides improved patient safety, which enables vitrectomy be safely and efficiently performed independent of other ocular procedures. For example, the sharp tip 208 of the shaft 206 of the vitrector 204 allows sclerotomy to be performed without removal of the conjunctiva or prior insertion of a trocar. In addition, the diameter of the shaft 206 of the vitrector 204 is sized to allow for removal of the vitrector 204 from the patient's eye without requiring sutures to close the sclerotomy. Further, the decreased length of the shaft 206 of the vitrector 204 compared to the shaft length of traditional vitrectors increases the overall strength and rigidity of the shaft 206 compared to the shafts of traditional vitrectors, which thereby improves patient safety by reducing the chance of iatrogenic damage to the device or the eye itself during insertion, use, and removal from the eye. In addition, the decreased length of the shaft 206 of the vitrector 204 compared to the shaft length of traditional vitrectors also reduces the risk of inserting the vitrector 204 too far into the eye, which helps prevent inadvertent contact of the vitrector 204 with the distal eyewall and thus reduces the risk of iatrogenic retinal damage. As a result, the vitrector 204 enables improved safety and patient outcomes in performing vitrectomies independently of other ocular procedures.

In addition, while the vitrector 204 has been described as being used to remove floaters from the vitreous of the patient's eye, in some implementations, the vitrector 204 can be used to remove other materials from the patient's eye. For example, the vitrector 204 can be used to remove cortical cataract material from a patient's eye by inserting the shaft 206 of the vitrector 204 into the patient's eye with the needle tip portion 208 of the vitrector 204 aimed toward cortical cataract material and aspirating and removing the cortical cataract material from the patient's eye using the aspiration line 214 of the vitrector 204. In addition, if necessary, the cutter 210 can be used to cut the cortical cataract material before aspirating the cortical cataract material from the patient's eye.

In some implementations, the vitrector 204 can be used to remove anterior or posterior capsular remnants from a patient's eye. For example, following cataract surgery, posterior capsular remnants or anterior capsular remnants may become free floating within the patient's eye and obstruct the patient's vision. Removal of anterior or posterior capsular remnants is commonly performed during pediatric cataract surgery, during surgery for traumatic cataract or injury, and during routine cataract surgeries that result in iatrogenic damage to the anterior or posterior capsule. The vitrector 204 can be used to remove capsular remnants by inserting the shaft 206 of the vitrector 204 into the patient's eye with the needle tip portion 208 of the vitrector 204 aimed toward the capsular remnants and aspirating and removing the capsular remnants from the patient's eye using the aspiration line 214 of the vitrector 204. In addition, if the capsular remnants are large, the cutter 210 can be used to cut the large capsular remnants into smaller pieces before aspirating the capsular remnants from the patient's eye through the aspiration line 214.

In some implementations, the vitrector 204 can be used to remove material from a patient's eye that is present due to intraocular medications or trauma to the patient's eye. For example, the vitrector 204 can be used to remove scar tissue, blood, or particulate matter that is present the patient's eye, for example, as a result of intraocular medications or trauma to the patient's eye. To remove material present in a patient's eye due to medications or trauma, such as blood or scar tissue, the shaft 206 of the vitrector 204 is inserted into the patient's eye with the needle tip portion 208 of the vitrector 204 aimed toward the material to be removed, and the cutter 210 is used to cut the material, if necessary. The material can then be aspirated and removed from the patient's eye using aspiration line 214.

In some implementations, the vitrector 204 can be used to perform a vitreous biopsy. For example, the aspiration line 214 of the vitrector 204 can be fluidly coupled to a specimen collection container, and material in the vitreous cavity can be biopsied by the vitrector 204 and provided to the specimen collection container coupled to the aspiration line 214. To perform a vitreous biopsy, the shaft 206 of the vitrector 204 is inserted into the vitreous cavity of the patient's eye with the needle tip portion 208 of the vitrector 204 aimed toward the material to be biopsied. The material to be biopsied can then be cut by the cutter 210, if necessary, and aspirated through the aspiration line 214 of the vitrector 204 into the specimen collection container coupled to the aspiration line 214.

While the cutter 210 of the vitrector 204 has been described as a pneumatically driven guillotine cutter, other suitable types of cutting devices configured to cut or sever tissue can be incorporated into the shaft 206 of the vitrector 204 to cut and remove material from the eye.

A number of embodiments have been described. Nevertheless, it will be understood that various modifications may be made without departing from the spirit and scope of the following claims.

REFERENCE NUMBER KEY

100—Conventional, prior art vitrector system
102—Light pipe of vitrector system 100
104—Conventional vitrector
204—Vitrector of present disclosure
205—Intraocular lens
206—Shaft of vitrector 204
207—Hand piece of vitrector 204
208—Sharp pointed tip portion of vitrector 204
210—Pneumatically driven guillotine cutter
212—Pneumatic line for fluidically driving guillotine cutter 201
214—Aspiration line for aspirationally removing floaters from the vitreous humor

What is claimed:

1. A vitrector for removing material from an eye, comprising:
- a hand piece;
- a shaft configured to be inserted into the eye, the shaft coupled at a first end to a first end of the hand piece, the shaft having a sharp second end opposite the first end of the shaft, the sharp second end of the shaft configured for piercing a pars plana of the eye and a sclera of the eye, wherein:

a total length of the shaft, measured from the first end of the shaft to the sharp second end of the shaft, is configured to be inserted into the eye and is between 0.5 inches and 0.5625 inches;

a diameter of the shaft along the total length of the shaft is approximately 27 gauge;

the shaft is configured to reach a mid-vitreous portion of the eye when the shaft is inserted into the eye; and the shaft has an inherent stiffness sufficient to pierce the pars plana and sclera of the eye without prior insertion of a trocar; and a cutting device positioned within the shaft and configured for removing the material from the eye.

2. The vitrector of claim 1, wherein the cutting device is a pneumatically driven guillotine cutter.

3. The vitrector of claim 2, wherein the pneumatically driven guillotine cutter is fluidly coupled to a source of pneumatic air for driving the pneumatically driven guillotine cutter.

4. The vitrector of claim 3, further comprising a pneumatic line configured to fluidly couple the cutting device to the source of pneumatic air.

5. The vitrector of claim 4, wherein the pneumatic line is coupled to a second end of the hand piece opposite the first end of the hand piece.

6. The vitrector of claim 3, wherein the source of pneumatic air is a phacoemulsification machine.

7. The vitrector of claim 1, further comprising:

an aspiration line fluidly coupled to the cutting device, wherein removing the material from the eye comprises drawing the material through the aspiration line.

8. The vitrector of claim 7, wherein the aspiration line is coupled to a second end of the hand piece opposite the first end of the hand piece.

9. The vitrector of claim 7, wherein the aspiration line is fluidly coupled to a source of suction.

10. The vitrector of claim 1, wherein:

the shaft comprises an elongate body coupled at a first end to the first end to the hand piece; and the sharp second end of the shaft comprises a needle tip coupled to a second end of the elongate body opposite the first end of the elongate body.

11. The vitrector of claim 10, wherein the needle tip is configured to be positioned in the mid-vitreous portion of the eye behind an intraocular lens implanted in the eye.

12. The vitrector of claim 1, wherein:

the material comprises one or more vitreous floaters; and the cutting device is configured to sever the one or more vitreous floaters from a vitreous cavity of the eye.

13. A method for removing material from an eye, the method comprising:

forming a single opening through a pars plana of the eye and a sclera of the eye using a sharp point of a shaft of a vitrector;

cutting the material using a cutting device incorporated within the shaft; and removing the material from the eye using the vitrector, wherein:

the vitrector comprises a hand piece;

the shaft is configured to be inserted in the eye;

the shaft is coupled at a first end to a first end of the hand piece;

the shaft has a sharp second end opposite the first end of the shaft, the sharp second end of the shaft configured for piercing the pars plana of the eye and the sclera of the eye;

the shaft has a total length, measured from the first end of the shaft to the sharp second end of the shaft, that is configured to be inserted into the eye and is between 0.5 inches and 0.5625 inches;

a diameter of the shaft along the total length of the shaft is approximately 27 gauge;

the shaft is configured to reach a mid-vitreous portion of the eye when the shaft is inserted into the eye; and the shaft has an inherent stiffness sufficient to pierce the pars plana and sclera of the eye without prior insertion of a trocar.

14. The method of claim 13, further comprising:

fluidly coupling a source of pneumatic air to the cutting device.

15. The method of claim 14, wherein:

the cutting device comprises a pneumatically driven guillotine cutter; and cutting material from the eye using the cutting device comprises pneumatically driving the pneumatically driven guillotine cutter using the source of pneumatic air.

16. The method of claim 13, further comprising:

fluidly coupling an aspiration line to the cutting device.

17. The method of claim 16, wherein removing the material from the eye using the vitrector comprises drawing the material through the aspiration line.

18. The method of claim 13, wherein:

the material comprises one or more floaters; and removing the material from the eye using the vitrector comprises removing the one or more floaters from a vitreous cavity of the eye.

19. The method of claim 13, further comprising:

prior to forming the single opening through the pars plana of the eye and the sclera of the eye, implanting an intraocular lens in the eye.

20. The method of claim 19, wherein the intraocular lens is implanted in the eye during a cataract surgery.

* * * * *